United States Patent
Kopperschmidt

(10) Patent No.: US 11,167,071 B2
(45) Date of Patent: Nov. 9, 2021

(54) SYSTEM AND METHOD FOR DETECTING AN OPERATING STATE OR A COURSE OF TREATMENT IN A BLOOD TREATMENT

(71) Applicant: FRESENIUS MEDICAL CARE DEUTSCHLAND GMBH, Bad Homburg (DE)

(72) Inventor: Pascal Kopperschmidt, Dittelbrunn (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 612 days.

(21) Appl. No.: 16/062,390

(22) PCT Filed: Dec. 8, 2016

(86) PCT No.: PCT/EP2016/080294
§ 371 (c)(1),
(2) Date: Jun. 14, 2018

(87) PCT Pub. No.: WO2017/102553
PCT Pub. Date: Jun. 22, 2017

(65) Prior Publication Data
US 2018/0361051 A1    Dec. 20, 2018

(30) Foreign Application Priority Data
Dec. 15, 2015 (DE) .................. 10 2015 016 271.3

(51) Int. Cl.
*A61M 1/36*     (2006.01)
*G16H 40/63*    (2018.01)
(Continued)

(52) U.S. Cl.
CPC ............ *A61M 1/3607* (2014.02); *A61M 1/14* (2013.01); *A61M 1/3656* (2014.02); *G16H 40/20* (2018.01);
(Continued)

(58) Field of Classification Search
CPC .. A61M 1/3607; A61M 1/14; A61M 2205/18; A61M 2205/3317;
(Continued)

(56) References Cited

U.S. PATENT DOCUMENTS 6,775,577 B2   8/2004   Crnkovich et al.
7,078,911 B2   7/2006   Cehelnik
(Continued)

FOREIGN PATENT DOCUMENTS

DE   19845027     4/2000
DE   102004011264  9/2004
(Continued)

OTHER PUBLICATIONS

Berührungslose Gestern-und Körpererkennung in der Diagnostick, "Jeder Atemzug wird erkannt," medizin & technic, Jun. 2012, 3 pp., URL: http:/www.medizin-und-technik.de/, (with Machine Translation).
(Continued)

*Primary Examiner* — Leslie R Deak
(74) *Attorney, Agent, or Firm* — Jacobson Holman, PLLC

(57) ABSTRACT

A computer-implemented method and a computer system are disclosed. The computer system (200, 300) is suitable for detecting an operating state of a blood treatment machine (100, 201, 202, 20 . . . , 20n) or of a course of treatment in a blood treatment or a deviation from an ideal or uncomplicated operating state or a course of treatment. The computer system comprises a first interface (20, 312), which is
(Continued)

adjusted to receive an operating parameter monitoring signal, wherein the operating parameter monitoring signal represents a time-dependent signal of a sensor for monitoring an operating parameter of the blood treatment machine or a signal derived from the time-dependent signal of the operating parameter, and a second interface (20, 312), which is adjusted to receive a user response signal, wherein a user response signal represents a signal of a user input with respect to the operating state or the course of treatment or the deviation from the ideal or uncomplicated course of treatment or operating state of a blood treatment performed using the blood treatment machine. The computer system additionally comprises an evaluation unit (40, 213), which is adjusted to generate allocation data or reference data, establishing a correlation between a determined user response and a respective operating parameter monitoring signal, a memory unit, which is configured to save the allocation data and reference data, wherein the evaluation unit is also adjusted to compare a determined operating parameter monitoring signal with the allocation data or reference data to derive from this an operating state, a course of treatment or a deviation from an ideal or uncomplicated operating state or course of treatment of the blood treatment machine or a typical user response thereto.

18 Claims, 4 Drawing Sheets

(51) Int. Cl.
*G16H 40/20* (2018.01)
*A61M 1/14* (2006.01)

(52) U.S. Cl.
CPC ......... *G16H 40/63* (2018.01); *A61M 2205/18* (2013.01); *A61M 2205/3317* (2013.01); *A61M 2205/3368* (2013.01); *A61M 2205/50* (2013.01); *A61M 2205/502* (2013.01); *A61M 2230/207* (2013.01); *A61M 2230/30* (2013.01)

(58) Field of Classification Search
CPC .... A61M 2205/3368; A61M 2230/207; A61M 2230/30; A61M 2205/502; G16H 40/63; G16H 40/20
See application file for complete search history.

(56) References Cited

U.S. PATENT DOCUMENTS

| | | | |
|---|---|---|---|
| 7,539,533 B2 | 5/2009 | Tran | |
| 7,973,667 B2 | 7/2011 | Crnkovich et al. | |
| 8,110,104 B2 | 2/2012 | Crnkovich et al. | |
| 8,323,503 B2 | 12/2012 | Levin et al. | |
| 8,487,881 B2 | 7/2013 | Keena | |
| 8,970,503 B2 | 5/2015 | Christie et al. | |
| 2001/0027331 A1 | 10/2001 | Thompson | |
| 2004/0133444 A1 | 7/2004 | Defaix et al. | |
| 2004/0193413 A1 | 9/2004 | Wilson et al. | |
| 2004/0220832 A1 | 11/2004 | Moll et al. | |
| 2006/0200260 A1 | 9/2006 | Hoffberg et al. | |
| 2006/0289342 A1 | 12/2006 | Sugioka et al. | |
| 2007/0041626 A1 | 2/2007 | Weiss et al. | |
| 2007/0112603 A1 | 5/2007 | Kauthen et al. | |
| 2009/0030729 A1 | 1/2009 | Doyle | |
| 2009/0095679 A1 | 4/2009 | Demers et al. | |
| 2009/0259960 A1 | 10/2009 | Steinle et al. | |
| 2010/0066676 A1 | 3/2010 | Kramer et al. | |
| 2010/0137693 A1 | 6/2010 | Porras et al. | |
| 2010/0143192 A1 | 6/2010 | Myrick et al. | |
| 2011/0087499 A1 | 4/2011 | Menon et al. | |
| 2011/0105979 A1 | 5/2011 | Schlaeper et al. | |
| 2011/0157480 A1 | 6/2011 | Curl | |
| 2011/0164163 A1 | 7/2011 | Bilbrey et al. | |
| 2012/0212455 A1 | 8/2012 | Kloeffel | |
| 2013/0018355 A1 | 1/2013 | Brand et al. | |
| 2013/0131574 A1 | 5/2013 | Cosentino et al. | |
| 2013/0211206 A1 | 8/2013 | Sands et al. | |
| 2013/0249855 A1 | 9/2013 | Zhang | |
| 2013/0267883 A1 | 10/2013 | Medrano | |
| 2013/0274642 A1 | 10/2013 | Soykan et al. | |
| 2013/0297330 A1 | 11/2013 | Kamen et al. | |
| 2014/0180711 A1 | 6/2014 | Kamen et al. | |
| 2014/0184422 A1 | 7/2014 | Mensinger et al. | |
| 2014/0266983 A1 | 9/2014 | Christensen | |
| 2014/0267003 A1 | 9/2014 | Wang et al. | |
| 2015/0045713 A1* | 2/2015 | Attalah | A61M 1/14 604/5.04 |
| 2015/0253860 A1 | 9/2015 | Meries | |

FOREIGN PATENT DOCUMENTS

| | | |
|---|---|---|
| DE | 102007006566 | 8/2008 |
| DE | 102011011767 | 8/2012 |
| DE | 102011053935 | 3/2013 |
| DE | 102013111084 | 4/2015 |
| EP | 2237131 | 10/2010 |
| EP | 2597584 | 5/2013 |
| WO | WO 2008/042219 | 4/2008 |

OTHER PUBLICATIONS

Please do not touch, "Berührungslose Interaktion anhand von 3-D Bilddaten," www.inspect.online.com, INSPECT Jul. 2011; URL: http:/www.gestigon.de/uploads.mediaGestigon_INS0711.pdf, (with Machine translation).

Fresenius Medical Care "2008T Hemodialysis Machine Operator's Manual" P/N 490122 Rev I, May 9, 2012, p. 222.

\* cited by examiner

SYSTEM AND METHOD FOR DETECTING AN OPERATING STATE OR A COURSE OF TREATMENT IN A BLOOD TREATMENT

TECHNICAL FIELD

The invention relates to a system and a method, in particular a computer system, a blood treatment system and a computer-implemented method for recognizing an operating state or a course of treatment or a deviation from an ideal or uncomplicated operating state or course of treatment in a blood treatment, in particular in an extracorporeal blood treatment.

BACKGROUND

To remove substances that must be eliminated in the urine and for withdrawal of fluid in chronic renal failure, there are various known methods of treatment of blood by mechanical treatment of blood. In hemodialysis, diffusive mass transport through the semipermeable membrane of the filter is predominant, whereas in hemofiltration there is convective mass transport through the filter membrane. Hemodiafiltration is a combination of these two methods. When speaking of dialysis below, this term should be understood to include both a plain dialysis treatment as well as a hemodiafiltration.

Therapeutic apheresis is another blood treatment method for removing unwanted substances from blood, in which whole blood is separated from plasma.

The known devices for carrying out the aforementioned blood treatment methods have an extracorporeal blood circulation and a blood treatment unit. The extracorporeal blood circulation comprises an arterial blood line, which supplies blood taken from the patient to a blood treatment unit, and a venous blood line, which carries treated blood away from the blood treatment unit.

Blood to be treated is taken from the patient through a patient access, and treated blood is returned to the patient through the same access.

In dialysis, the blood treatment unit is designed as a filter unit having a blood chamber, which is connected by a semipermeable membrane to the dialysis fluid chamber. The dialysis fluid chamber is connected to the dialysis fluid system. The dialysis fluid system comprises a dialysis fluid supply line, which carries fresh dialysate to the dialysis fluid chamber as well as a dialysis fluid discharge line leading away from the dialysis fluid chamber.

For monitoring a course of a dialysis treatment for whether it is free of complications, a dialysis machine is typically equipped with a variety of sensors. Thus, conductivity sensors for measuring the electrical conductivity of the dialysate are provided in the dialysis fluid supply line and in the dialysis fluid discharge line. A comparison of the conductivity values measured with the two sensors allows an inference as to the purification performance (clearance).

Blood temperature sensors and blood pressure sensors are typically provided in the arterial and venous blood lines in the extracorporeal blood circulation.

Automatic analysis of the sensor signals is typically based on whether they fall below or exceed threshold values that have been set for monitoring the sensor signals. Setting the threshold values requires a skilled operator and is often susceptible to errors.

The blood treatment carried out by the caregiving medical staff is based largely on established routines. The interpretation of the complex sensor signals and trends therein by the user may constitute a challenge for the user if it is an atypical situation. The possibility of a faulty user response as a result constitutes a risk for the patient.

The object of the present invention is therefore to solve at least one of the problems defined above and to provide a computer-supported system, which will permit a reliable detection of an operating state or a course of treatment in a blood treatment.

SUMMARY

This object is achieved by a computer system according to the following description, a blood treatment system according the following description, a computer-implemented method according to the following description, a computer program product according to the following description and a computer program according to the following description. Advantageous embodiments are defined in the following description.

One embodiment relates to a computer system for detection of an operating state or a course of treatment or a deviation from an ideal or uncomplicated operating state of a treatment machine or of a course of treatment in a blood treatment. Examples of a blood treatment machine include a plasmapheresis machine, a hemodialysis, machine or a hemofiltration machine.

The computer system comprises a first interface, which is adjusted to receive an operating parameter monitoring signal, wherein the operating parameter monitoring signal represents a time-dependent signal of a sensor for monitoring an operating parameter of the blood treatment machine or a signal derived from the time-dependent signal of the operating parameter.

The formation of a derived signal may include the fact that a time segment or a time window cut out of the time-dependent signal of the operating parameter, approximately by means of a window operation, in particular by employing a weighted window function. Forming a derived signal may also include extracting features from the time-dependent signal of the operating parameter or subjecting the time-dependent signal of the operating parameter to a filter operation. The filter operation may be linear or non-linear. Examples of a linear filter operation include a Fourier transform or a wavelet transform.

The operating parameter may be, for example, a blood flow rate, a blood temperature, a blood hematocrit in an extracorporeal blood circulation, a dialysate temperature in hemodialysis, a conductivity of the dialysate in hemodialysis, a blood pressure in an extracorporeal blood circulation, in particular an arterial blood pressure, a venous blood pressure or a combination of an arterial blood pressure and a venous blood pressure, or the power consumption by an actuator, in particular a blood pump. An operating parameter monitoring signal in the sense of the present disclosure may be formed by combining a plurality of operating parameter monitoring signals.

The computer system also comprises a second interface, which is adjusted to receive a user signal, wherein a user response signal represents a signal of a user input with regard to the operating state or the course of treatment or the deviation from an ideal course of treatment or an uncomplicated course of treatment or operating state of a blood treatment performed with the blood treatment machine. The first and second interfaces may be embodied as one interface.

The operating state or course of treatment or the deviation from an ideal or uncomplicated operating state or course of treatment may relate to the patient, the blood treatment machine or the system comprised of patient and blood treatment machine. Examples include disconnection of the venous needle from the patient's access, clotting of the dialysis machine membrane, recirculation of the treated blood in the arterial part of the extracorporeal blood circulation or a hypertensive crisis.

The user response signal may include a conventional user response as part of a blood treatment such as adjusting a blood flow rate or the ultrafiltration rate, initiating the administration of an electrolyte or the like.

The user response may be a manually triggered alarm or a manually triggered stoppage of treatment.

Alternatively, the user response signal may indicate explicitly the operating state or the course of treatment or the deviation from an ideal or uncomplicated course of treatment or operating state such as detection of a hypertensive crisis, detection of a needle dislocation or the like.

The user response may occur during an ongoing treatment or because of an analysis of historical treatment data such, as a historical operating parameter monitoring signal. The user response may take place through a patient, through a person administering the treatment or through an expert.

The user response signal may be provided with a time stamp, which indicates the point in time of the user response or a user input with respect to the course of treatment.

To the extent to which a time segment or time window can be cut out of the time-dependent signal of the operating parameter, this time segment or time window may be selected, so that the point in time of the user response or user input occurs in the segment or the time window or next to it.

The computer system advantageously comprises a memory unit, which is configured to store a plurality of user response signals and operating parameter monitoring signals with respect to one another.

The computer system additionally comprises an evaluation unit, which is adjusted to generate allocation data or reference data, establishing a correlation between a determined user response and one or more corresponding operating parameter monitoring signals.

The allocation data and reference data may be in the form of a function, which establishes mapping of an operating parameter monitoring signal onto a corresponding user response.

The corresponding operating parameter monitoring signal may be a typical operating parameter monitoring signal, which fits with the specific user response. The respective operating parameter monitoring signal may represent a plurality of operating parameter monitoring signals, which fit with a determined user response or an averaging of a plurality of operating parameter monitoring signals, which fit with a determined user response. The averaging may be a linear or nonlinear averaging.

The allocation data and reference data can be created by taking into account a machine-specific parameter of the blood treatment machine, for example, in the sense that there is a standardization which takes the machine-specific parameter into account.

The creation of the allocation data or reference data may be based on the use of a learning algorithm, into account on the use of a neural network, in which the allocation between a determined user response and a respective operating parameter monitoring signal is learned from a plurality of data tuples. A data tuple comprises a determined user response and a determined operating parameter monitoring signal, which was recorded at the time of the user response.

The evaluation unit is also adjusted to compare a determined operating parameter monitoring signal, preferably an instantaneously recorded operating parameter monitoring signal of an ongoing blood treatment, with the allocation data or reference data to derive from this an operating state or a course of treatment or a deviation from an ideal or uncomplicated operating state or course of treatment of the blood treatment machine, in particular an instantaneous operating state or course of treatment or an instantaneous deviation from an ideal or uncomplicated operating state of the blood treatment machine or the course of treatment of the ongoing blood treatment or to derive a typical user response thereto.

The determined operating parameter monitoring signal and the corresponding typical user response can be used in a type of iterative learning process for generating additional and/or improved allocation data and reference data.

The instantaneous operating state or the instantaneous deviation from an ideal or uncomplicated operating state may be linked to a typical or adequate user response thereto, for example, when the instantaneous operating state is an alarm state and the adequate user response is an interruption in the blood treatment.

The blood treatment machine may be configured so that a recommendation to perform the typical or adequate user response is output to the user via a user interface.

The blood treatment machine may also be configured, so that an adaptation of the operating parameters that corresponds to the typical or adequate user response, for example, a reduction in the blood flow rate or a treatment interruption, is performed automatically.

One embodiment relates to a computer-implemented method for detecting an operating state of a blood treatment machine or a course of treatment in a blood treatment performed using the blood treatment machine or a deviation from an ideal or uncomplicated operating state or a course of treatment. The computer-implemented method comprises the following steps:

receiving an operating parameter monitoring signal, wherein the operating parameter monitoring signal represents a time-dependent signal of a sensor for monitoring an operating parameter of the blood treatment machine or a signal derived from the time-dependent signal of the operating parameter, receiving a user response signal, wherein the user response signal represents a signal of a user input with respect to the operating state or the course of treatment or the deviation from an ideal or uncomplicated operating state or course of treatment, saving a plurality of user response signals and operating parameter monitoring signals with respect to one another, generating allocation data or reference data that establishes an allocation or correlation of a determined user response to/with an allocated operating parameter monitoring signal, saving the allocation data or reference data, receiving a determined operating parameter monitoring signal at a determined point in time during the blood treatment, and comparing the operating parameter monitoring signal thereby determined with the allocation data or reference data to derive therefrom an instantaneous operating state or course of treatment or an instantaneous deviation from an ideal or uncomplicated operating state or course of treatment at the determined point in time or a typical user response thereto.

The same modifications can be applied to the computer-implemented method as to the computer system that is described.

DETAILED DESCRIPTION OF THE DRAWINGS

Figure 1:
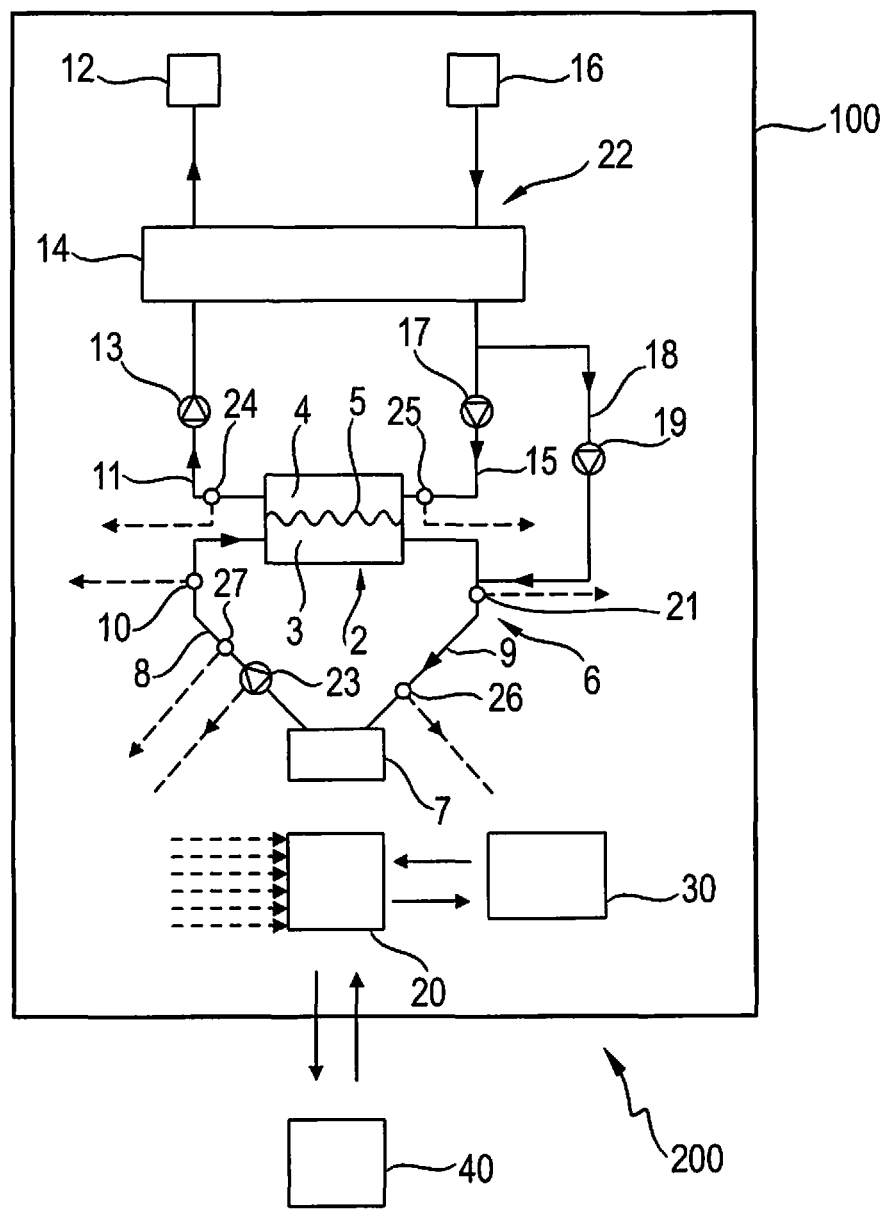
FIG. 1 shows a dialysis system with a hemodialysis machine in one embodiment according to the present teaching.

FIG. 1 shows a dialysis system 200 with a dialysis machine 100 and a central monitoring unit 40.

The dialysis machine 20 has a blood treatment unit 2 (dialysis machine) with a dialysis fluid chamber 4 in a dialysis fluid circulation 22 which is separated by a semipermeable membrane 5 from a blood chamber 3 in a blood circulation.

Prepared dialysis fluid is supplied by a dialysis fluid source 16 and conveyed by a dialysis liquid pump 17 through the dialysis fluid supply line 15 into the dialysis fluid chamber 4. Spent dialysis fluid is sent by the dialysis fluid pump 13 through the dialysis fluid discharge line 11 away from the dialysis fluid chamber 4 and to a drain 12. In an alternative embodiment, the spent dialysis fluid can also be processed.

In the dialysis fluid chamber 4, the dialysis fluid absorbs the substances which must be eliminated in urine and which cross over the dialysis machine membrane 5 from the blood in the blood chamber 3 into the dialysis fluid.

A balancing unit 14 ensures the balance between fresh and spent dialysis fluid. Flow sensors, scales or balancing chambers are used for this balancing. In the latter case, it may not be necessary to provide a second dialysis fluid pump.

In the optional embodiment of a hemodiafiltration machine as presented here, a substituate line 18 over which filtered dialysis fluid conveyed with a substituate pump 19 is added as substituate to the blood that is to be treated. To simplify the diagram, the filter required for this is not shown. The substitution fluid may be added downstream from the dialysis machine, as shown here (post-dilution), or upstream from the dialysis machine (pre-dilution). A combination of these methods is also possible.

The blood to be treated is taken from the patient 7 via a patient access and is sent by the blood pump 23 over the arterial blood line 8 of the extracorporeal blood circulation 6 to the blood chamber 3 of the dialysis machine 2, where it is purified of unwanted blood constituents and returned to the patient 7 over the venous blood line 9.

The dialysis machine 100 has various sensors for monitoring the blood treatment. Thus, a conductivity sensor 25 may be provided in the dialysis fluid supply line in the dialysis fluid circulation in order to determine the conductivity in the fresh dialysate. A conductivity sensor 24 may be provided in the dialysis fluid discharge line to determine the conductivity in the spent dialysate. The signal of the conductivity sensor 24 and the signal of the conductivity sensor 25 or a combination of the signals of the conductivity sensor 24 and 25 then form an operating parameter monitoring signal.

Dialysance is an operating parameter monitoring signal that is based on the conductivity sensors 24 and 25. The background to this is provided by the monitoring of the blood purification performance, i.e., the clearance, which is important in monitoring the extracorporeal blood treatment. The clearance K is defined as the proportion of the blood flow through the blood chamber that is purified completely of toxins, in particular urea. In practice, dialysance is determined instead of clearance. In dialysance, the permeability of the filter membrane for electrolytes contained in the dialysis fluid is measured. To do so, the concentration of one or more electrolytes in the dialysis fluid in the dialysis fluid circulation upstream from the dialysis fluid chamber 4 is adjusted with the help of a bolus-forming agent (not shown) and the resulting change in concentration downstream from the dialysis fluid chamber is determined. The adjusted concentration of one or more electrolytes both upstream and downstream from the dialysis fluid chamber has an influence on the conductivity of the dialysis fluid and is measured by the conductivity sensors 25 upstream from the dialysis fluid chamber 4 and the downstream conductivity sensors 24. Such a method for determining the clearance during the ongoing treatment is referred to as online clearance monitoring and is disclosed in European Patent EP 0 911 043 by the present applicant, the disclosure content of which is fully included in the present patent application. A commercial method based on this principle is distributed by the company Fresenius Medical Care Deutschland GmbH under the designation OCM (online clearance monitor).

In the extracorporeal blood circulation 6, an arterial pressure sensor 27 and an arterial temperature sensor 10 may be provided as sensors in the arterial blood line, and a venous pressure sensor 26 plus a venous temperature sensor 21 may be provided in the venous blood line 9. A power consumption signal is supplied by the blood pump 23. The signal of the venous pressure sensor 26, the signal of the arterial pressure sensor 27, the signal of the venous temperature sensor 21, the signal of the arterial temperature sensor 10 and the power consumption signal of the blood pump 23 are each a function of time and each forms an operating parameter monitoring signal. In addition, a hematocrit sensor (not shown), which supplies an operating parameter monitoring signal may also be provided in the arterial and/or venous blood line.

During an ongoing treatment, operating parameter monitoring signals are transmitted to the central processing unit 20, where they are recorded and sent to the central monitoring unit 40 after the end of the treatment. Alternatively, operating parameter monitoring signals are transmitted continuously during the ongoing treatment to the central monitoring unit 40. The central monitoring unit 40 may comprise a databank.

The dialysis machine 100 has an input unit 30, with the help of which a user input can be performed pertaining to the blood treatment or the course thereof or a deviation from an ideal or uncomplicated course of treatment or operation of the dialysis machine. The user response may pertain to a conventional user input within the scope of the ongoing blood treatment, triggering of an alarm or stopping a treatment or reporting the cause of an alarm. The user input is forwarded to the central processing unit 20, where it is processed further. During the ongoing treatment or after the end of the treatment, a signal containing the user input is transmitted to the central monitoring unit.

Figure 3:
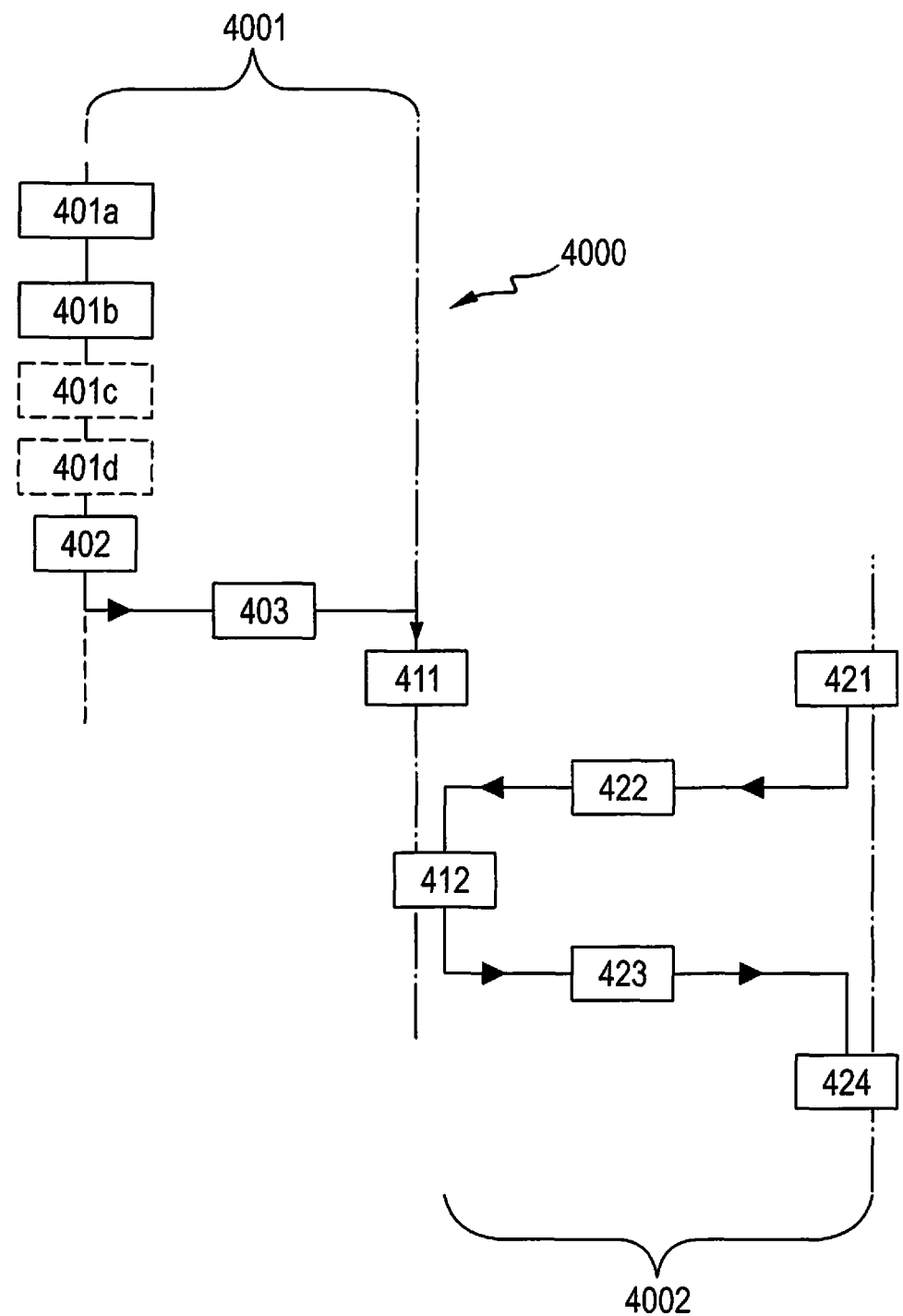
FIG. 3 shows a flow chart of a computer-implemented method in one embodiment according to the present teaching.

The user input and the corresponding allocated operating parameter monitoring signal are stored in the central monitoring unit and used in accordance with the data acquisition or learning phase 4001 described in conjunction with FIG. 3 and/or the monitoring phase 4002.

Figure 2:
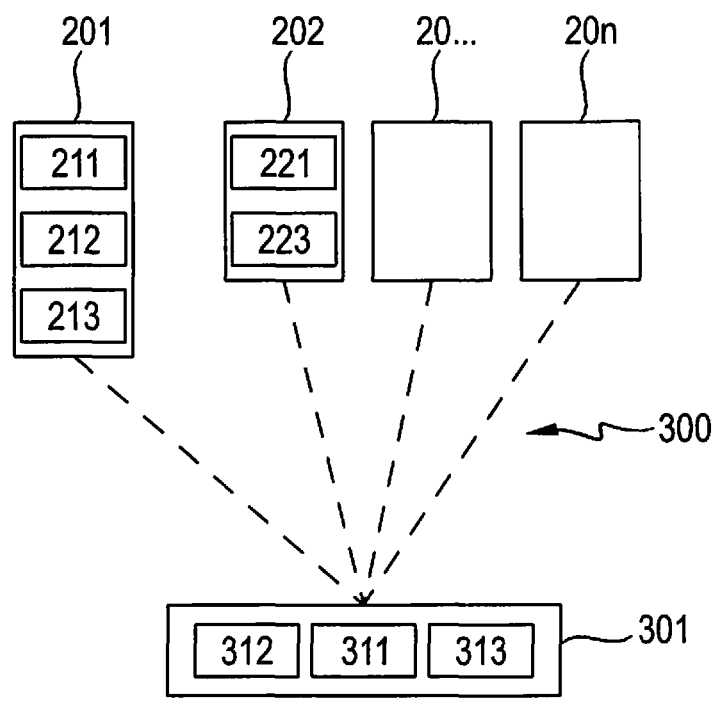
FIG. 2 shows a blood treatment system in one embodiment according to the present teaching.

FIG. 2 shows schematically a blood treatment system according to the present teaching.

The blood treatment system 300 has a plurality of blood treatment machines 201, . . . , 20n, whose operating parameters are monitored constantly.

The blood treatment machines 201, . . . , 20n each have at least one sensor 211 for monitoring an operating parameter of the blood treatment and for generating a time-dependent sensor signal or a signal derived from this signal.

In addition, the blood treatment machines 201, . . . , 20n each have at least one input/output unit 212, which performs a user input with regard to the operating state or the course of treatment or the deviation from an ideal or uncomplicated course of treatment or an operating state of a blood treatment performed by the blood treatment machine in an adjusted manner.

Blood treatment machines 201, . . . , 20n each also has an interface 213 for communication with the central unit 301 and for transmission of user inputs and sensor signals to the central unit 301.

The central unit 301 has an interface 312 for communication with the blood treatment machines 201, . . . , 20n and for receiving user inputs and sensor signals from the blood treatment machines.

The central unit 301 may be implemented as an individual system or as a distributed system. The central unit may be part of a client/server architecture and/or may be implemented as part of a cloud network. The central unit 301 has a memory unit 311, which is configured to store a plurality of user response signals and operating parameter monitoring signals with respect to one another and via an evaluation unit 313, which is adjusted to generate allocation data or reference data, establishing a correlation between a determined user response and a respective operating parameter monitoring signal. The memory unit is also adjusted to store the allocation data and reference data. The memory unit 311 may be embodied as a databank. The evaluation unit 313 has access to the allocation data and reference data stored in the memory unit 311.

The evaluation unit 313 is also adjusted to receive a determined operating parameter monitoring signal, which was recorded by one of the blood treatment machines 201, . . . , 20n at a determined point in time during the blood treatment, from one of the blood treatment machines, namely here the blood treatment machine 202, and to compare it with the allocation data or reference data to derive from this an operating state, a course of treatment or a deviation from an ideal or uncomplicated operating state or course of treatment at the determined point in time or a suitable user response thereto.

The central unit 301 is adjusted to return to an operating state, the course of treatment or the deviation from an ideal or uncomplicated operating state or course of treatment at the determined point in time or the suitable user response to the corresponding one of the blood treatment machines 201, . . . , 20n, namely to the blood treatment machine 202 here.

The blood treatment machine 202 is adjusted to respond in a suitable manner with a suitable user response to the operating state, the course of treatment or the deviation from an ideal or uncomplicated operating state or course of treatment at the determined point in time.

Therefore, the blood treatment machine 202 has an output unit 221 for output of an alarm in response to the derived deviation from an ideal or uncomplicated operating state or course of treatment of the blood treatment machine or the typical user response.

In addition, the blood treatment machine 202 has a control unit 223 for controlling the blood treatment machine in response to the derived deviation from an ideal or uncomplicated operating state or course of treatment of the blood treatment machine or the typical user response. In one embodiment, the control unit is adjusted to initiate an interruption of the blood treatment in response to the deviation.

FIG. 3 shows a flow chart of a computer-implemented method 4000 according to the invention for determining an operating state of a blood treatment machine, of a course of treatment in a blood treatment or the deviation from an ideal or uncomplicated operating state or course of treatment in a blood treatment or a suitable user response thereto.

The individual steps of the computer-implemented method can be carried out by the components of the dialysis system 200 (cf. FIG. 1) or by the components of the blood treatment system 300 (cf. FIG. 2).

The computer-implemented method 4000 comprises a data acquisition or learning phase 4001 and a monitoring phase 4002.

While performing a blood treatment with a blood treatment machine 201, . . . 20n, in particular a dialysis treatment with a dialysis machine 100, at least one operating parameter of the blood treatment machine is monitored continuously 401a, and its time-dependent course of a measurement signal of the monitored operating parameter is saved as the operating parameter monitoring signal 401b. The time-dependent measurement signal of the monitored operating parameter may be a time-dependent signal of a sensor of the blood treatment machine such as a connectivity signal of the fresh dialysate, a conductivity signal of the spent dialysate, a temperature signal of the arterial or venous blood temperature, a pressure signal of the arterial or venous temperature sensor or a power consumption signal of the blood pump or some other time-dependent measurement signal of an operating parameter.

With regard to the course of treatment or the deviation from an ideal or uncomplicated course of treatment or operating state during the blood treatment, there is a user input 402.

The user input 402 may represent a response by the user to a situation detected as part of an ongoing blood treatment, for example, a reduction in the blood flow rate, as a result of an increasing arterial pressure detected by the user. Other examples include a reduction in the ultrafiltration rate or initiation of administration of an electrolyte because of a detected hypertensive crisis.

The user input 402 may include a manually triggered alarm or a manually triggered stop of treatment.

Alternatively or additionally, an automatically generated alarm or a manually triggered alarm may be associated with a request to the user to specify a cause for the alarm. Thus the user may advantageously be offered a possibility of selection among various possible causes for the alarm that has occurred, for example, in the form of a drop-down menu. The user input 402 in this case comprises the statement of the cause for the alarm. The user input may be made by a caregiver or by the treated position. In one embodiment, the user input may be supplemented by a time stamp indicating the point in time of the user input with respect to the course of treatment, for example, the time elapsed since the start of the blood treatment.

After reaching the end of the treatment, the sensor signal recorded is transmitted 403 from the blood treatment machine to a central monitoring unit together with one or more user entries made during the blood treatment. Before the transfer to the central computer unit, the sensor signal may be subjected to a signal processing 401c and/or a feature extraction 401d. The signal processing may include a trend analysis of the sensor signal, for example, analysis of a long-term trend. In one embodiment, the signal processing 401c comprises a window operation in the range of the point in time of the user entries to generate a signal window (windowing) or the use of a linear or nonlinear filter. Examples of a linear operation include a Fourier transform of the signal window or a wavelet transform. In an alternative embodiment, signal processing 401c and/or feature extraction 401d may take place on the part of the central monitoring unit. In another alternative embodiment, the transfer 403 of the sensor signal to the central monitoring unit may take place continuously during the ongoing blood treatment.

In the central evaluation unit, allocation data and reference data, establishing an allocation or correlation between a determined user input and the corresponding sensor signal, are generated 411.

The sequence of steps 401a to 411 is advantageously run through as a data acquisition or learning phase 4001 for generating the allocation data and reference data for a plurality of treatments, preferably using a plurality of blood treatment machines 201, . . . , 20n. In the step of generating 411, the allocation data and reference data, the allocation between user input and sensor signal may take place in the form of a learning phase of a learning algorithm, preferably of a neural network. Expressed in simplified terms the allocation data or reference data establishes an allocation between a determined user input and a typical signal characteristic of a determined operating parameter (signal pattern) corresponding to this user input. For example, it has been found that the signal characteristic of the arterial blood pressure and the signal characteristic of the venous blood pressure in a dislocation of the venous needle both have a characteristic pattern. In this case the allocation data and reference data establish an allocation between this characteristic signal pattern and the deviation found by the user from the uncomplicated course of treatment in the form of a user input. The allocation may take place in such a way that a determined cause is allocated to the course of treatment or an adequate user response thereto, i.e., in the case of the dislocation of the venous needle, this would be the initiation of an immediate stoppage of treatment.

In one embodiment, the allocation data or reference data for a determined user input comprises a plurality of allocated signal patterns together with the statement of a frequency at which a determined signal pattern occurs or a probability distribution over various allocated signal patterns.

In an alternative embodiment, the allocation data and reference data for a determined signal pattern comprise a plurality of user responses, preferably associated with a probability distribution over the user responses, wherein the user response for which the greatest probability was indicated is preferably characterized as the most adequate user response.

In an alternative embodiment, the user input does not occur or does not occur exclusively online during the blood treatment but instead the recorded sensor data is investigated offline by an expert from the standpoint of detecting a deviation from an ideal or uncomplicated operating state or course of treatment and/or a cause of this deviation or an adequate response thereto. In this embodiment, this statement of the cause for the deviation or the response to it represents the user input, which is in turn allocated to the sensor signal and/or is correlated with it to generate allocation data or reference data as described above. In one embodiment, a different weight can be allocated by an expert to a user input in generating the allocation data and reference data, depending on the level of experience of the expert.

The allocation data and reference data may be used in a subsequent monitoring phase 4002 to monitor an ongoing blood treatment. For the blood treatment to be monitored, sensor data of an operating parameter is recorded continuously 421 and transmitted 422 to the central monitoring unit 40, 301 and received there. In the central monitoring unit, a comparison 412 of the transmitted sensor data or a segment, i.e., window thereof, is compared with the allocation data and reference data. If a similarity or a correlation in the pattern of the transmitted sensor signal or a segment thereof with a typical signal pattern contained in the allocation data or reference data is found then the allocated user input is derived from that. In one embodiment a correlation is found between a transmitted sensor signal and a typical sensor pattern of such a type that there is the highest correlation with the typical signal pattern in comparison with other signal patterns stored in the central monitoring unit.

In this way, a deviation from an ideal or uncomplicated course of treatment can be detected and/or the cause of this or an adequate user response to it can be ascertained. The user input detected or a deviation derived therefrom from an ideal or uncomplicated operating state or course of treatment of the blood treatment machine is/are transmitted 423 to the blood treatment machine. The blood treatment machine may respond 424 in a suitable way to the transmitted user input or the derived deviation from the ideal or uncomplicated operating state or course of treatment. The blood treatment machine can therefore output an alarm, implement a' treatment stoppage or an adjustment of treatment parameters in accordance with the user input detected.

Figure 4:
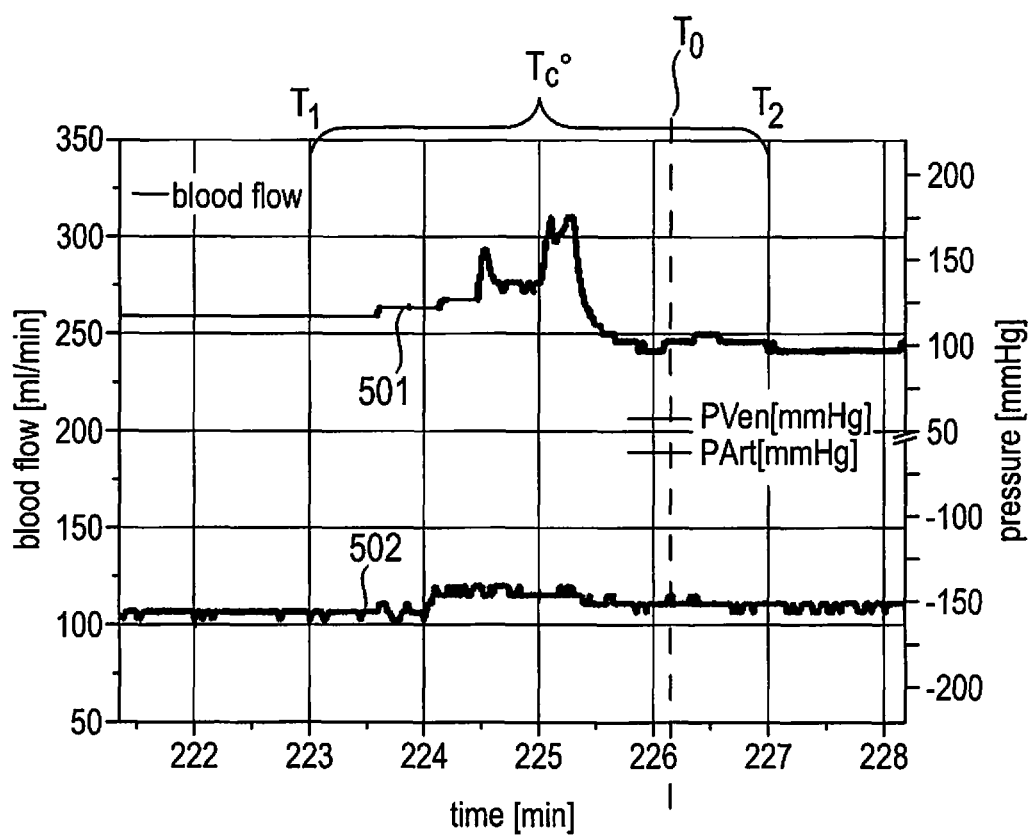
FIG. 4 shows the allocation between user input and signal pattern on the example of a venous pressure pattern and an arterial pressure pattern.

FIG. 4 shows the allocation between a user input and a signal pattern on the example of a venous and an arterial pressure pattern at the point in time of a venous needle dislocation in a blood treatment with a blood treatment machine 100 such as that described in conjunction with FIG. 4.

The time-dependent course of the signal of the venous pressure sensor 26 is labeled as 501, the time-dependent characteristics of the signal of the arterial pressure sensor 27 is labeled as 502. Between the point in time T1 and the point in time T2 a dislocation of the venous needle occurs. At the point in time T0, there is a user input such as initiation of a treatment stoppage and/or triggering of an alarm which is advantageously associated with the statement of a corresponding cause for the alarm.

According to, the user input at the point in time T0, a window is formed from the venous pressure signal and the arterial pressure signal (windowing) between the points in time T1 and T2. The signal windows of the venous pressure signal and of the arterial pressure signal together with the user input form an allocation data or reference data in the sense of the present disclosure.

The invention claimed is:

1. A computer system for detecting an operating state of a blood treatment machine or of a course of treatment in a blood treatment or a deviation from an ideal or uncomplicated operating state or course of treatment comprising:
    a first interface, which is configured to receive an operating parameter monitoring signal, wherein the operating parameter monitoring signal represents a time-dependent signal of a sensor for monitoring an operating parameter of the blood treatment machine or a signal derived from the time-dependent signal of the operating parameter, a second interface which is configured to receive a user response signal, wherein a user response signal represents a signal of a user input with respect to the operating state or the course of treatment or the deviation from the ideal or uncomplicated course of treatment or operating state of a blood treatment performed using the blood treatment machine, an evaluation unit, which is configured to generate allocation data or reference data, establishing a correlation between a determined user response and a respective operating parameter monitoring signal using a neural network, in which neural network the correlation between a determined user response and a respective operating parameter monitoring signal is learned from a plurality of data tuples, each data tuple comprising a determined user response and a determined operating parameter monitoring signal recorded at the time of the user response, a memory unit, which is configured to save the allocation data and reference data, wherein the evaluation unit is also configured to compare a determined operating parameter monitoring signal of an ongoing treatment with the allocation data or reference data to derive from this a typical user response thereto.

2. The computer system according to claim 1, wherein the evaluation unit is configured to use a learning algorithm, in particular a neural network in generating the allocation data or reference data.

3. A blood treatment system having at least one blood treatment machine for carrying out a blood treatment with at least one sensor for determining a time-dependent characteristic of an operating parameter during the blood treatment and having a computer system according to claim 1.

4. The blood treatment system according to claim 3, wherein the blood treatment machine is a dialysis machine and wherein the sensor is selected from a blood temperature sensor, a hematocrit sensor, a blood pressure sensor, a conductivity sensor to determine a conductivity of a dialysate or a sensor for determining the power consumption of an actuator.

5. The blood treatment system according to claim 3, wherein an evaluation unit is configured to the blood treatment machine to provide the user input signal with a time stamp indicating the point in time of the user input with respect to the course of treatment, and wherein the evaluation unit of the computer system or the evaluation unit of the blood treatment machine is configured to cut out a time segment or a time window from the time-dependent signal, and wherein the point in time of the user input lies in the time segment or time window or adjacent thereto.

6. The blood treatment system according to claim 3, having an input unit for input of a user response with respect to an operating state or a course of treatment or to a deviation from an ideal or uncomplicated operating state of the blood treatment machine or a deviation from an ideal or uncomplicated course of treatment of the blood treatment.

7. The blood treatment system according to claim 3, having an output unit for output of an alarm in response to the derived deviation from an ideal or uncomplicated operating state or course of treatment of the blood treatment machine or the typical user response.

8. The blood treatment system according to claim 3, having a control unit for controlling the blood treatment machine in response to the derived deviation from an ideal or uncomplicated operating state or course of treatment of the blood treatment machine or the typical user response.

9. The blood treatment system according to claim 8, wherein the control unit is configured to initiate an interruption in the blood treatment in response to the deviation.

10. A computer-implemented method for detecting an operating state of a blood treatment machine or of a course of treatment in a blood treatment or a deviation from an ideal or uncomplicated operating state or course of treatment, comprising:

receiving an operating parameter monitoring signal, wherein the operating parameter monitoring signal represents a time-dependent signal of a sensor for monitoring an operating parameter of the blood treatment machine or a signal derived from the time-dependent signal of the operating parameter, receiving a user response signal, wherein the user response signal represents a signal of a user input with respect to the operating state or the course of treatment or the deviation from an ideal or uncomplicated course of treatment or operating state of a blood treatment performed with the blood treatment machine, saving a plurality of user response signals and operating parameter monitoring signals with respect to one another, generating allocation data or reference data and establishing an allocation or correlation of a determined user input with an allocated operating parameter monitoring signal from a plurality of data tuples, each data tuple comprising a determined user response and a determined operating parameter monitoring signal recorded at the time of the user response, saving the allocated data and reference data, receiving a determined operating parameter monitoring signal of an ongoing treatment, and comparing the determined operating parameter monitoring signal of an ongoing treatment with the allocated data or reference data to derive from that a typical user response thereto.

11. The computer-implemented method according to claim 10, wherein the step of generating the allocation data or reference data comprises the following: using a learning algorithm, in particular a neural network.

12. The computer-implemented method according to claim 10, containing the following steps:

providing the user input signal with a time stamp indicating the point in time of the user input with respect to the course of treatment, forming a time window or a time segment of the time-dependent signal, wherein the point in time of the user input lies in the time window or the time segment or adjacent thereto.

13. The computer-implemented method according to claim 10, containing the following step: output of an alarm in response to the derived deviation from an ideal or uncomplicated operating state or course of treatment of the blood treatment machine or the typical user response.

14. The computer-implemented method according to claim 10, containing the following step: controlling the blood treatment machine in response to the derived deviation from an ideal or uncomplicated operating state or course of treatment of the blood treatment machine or the typical user response.

15. The computer-implemented method according to claim 14, wherein the step of controlling the blood treatment machine comprises the following: initiating an interruption in the blood treatment.

16. A computer program product comprising instructions, which carry out the computer-implemented method according to claim 10 when loaded into at least one memory module of a computer system and processing by at least one processor of the computer system.

17. The computer program comprising instructions for carrying out the computer-implemented method according to claim 10 when the computer program is carried out on a computer.

18. The blood treatment system according to claim 4, wherein the actuator is a blood pump.

\* \* \* \* \*